United States Patent [19]
Harris

[11] 3,939,842
[45] Feb. 24, 1976

[54] HEMORRHOIDAL DEVICE
[75] Inventor: Arthur M. Harris, Miami Shores, Fla.
[73] Assignee: Key Pharmaceuticals, Inc., Miami, Fla.
[22] Filed: Sept. 5, 1974
[21] Appl. No.: 503,335

[52] U.S. Cl. ............ 128/401; 128/303.12; 128/403
[51] Int. Cl.² ...................... A61F 7/12; A61B 17/36
[58] Field of Search ...... 128/303.12, 401, 360, 359, 128/341, 343, 403

[56] References Cited
UNITED STATES PATENTS

| | | | |
|---|---|---|---|
| 47,540 | 5/1865 | Gilbert | 128/343 X |
| 969,134 | 8/1910 | Cowie | 128/303.12 |
| 2,566,595 | 9/1951 | Cameron | 128/359 |
| 2,707,471 | 5/1955 | Koff | 128/341 |
| 3,826,242 | 7/1974 | Eggers | 128/341 |

Primary Examiner—Lawrence W. Trapp
Attorney, Agent, or Firm—Kenyon & Kenyon Reilly Carr & Chapin

[57] ABSTRACT

A disposable rectal insert of plastic material chemically inert to body fluids encapsulating a freezable medium having a freezing point of about 0° to 32°F. The insert has a small bulbous end for rectal insertion which is collapsible upon melting of the medium and compensating dilation of the other enlarged reservoir end maintains constant internal volume of the insert.

4 Claims, 7 Drawing Figures

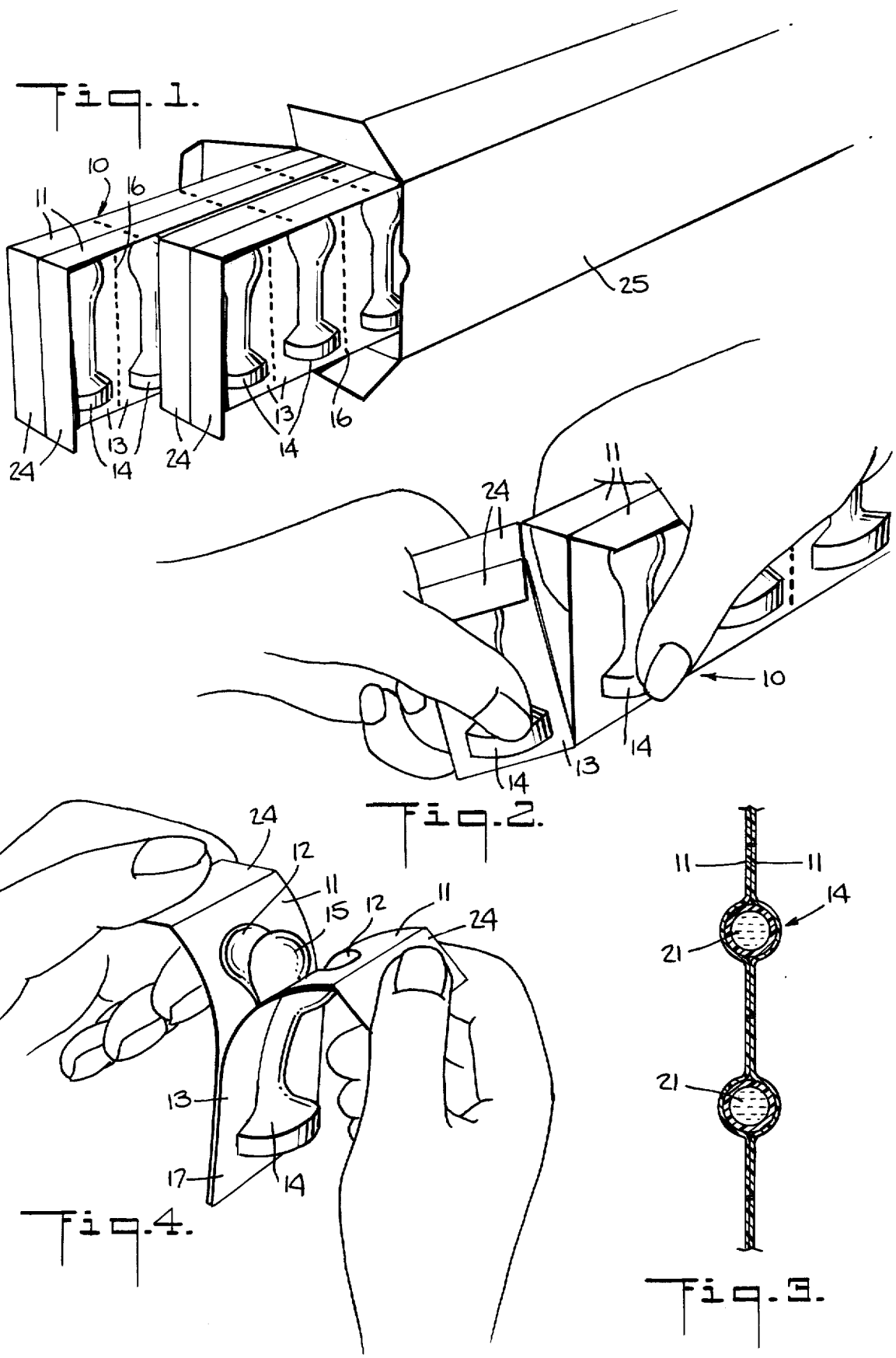

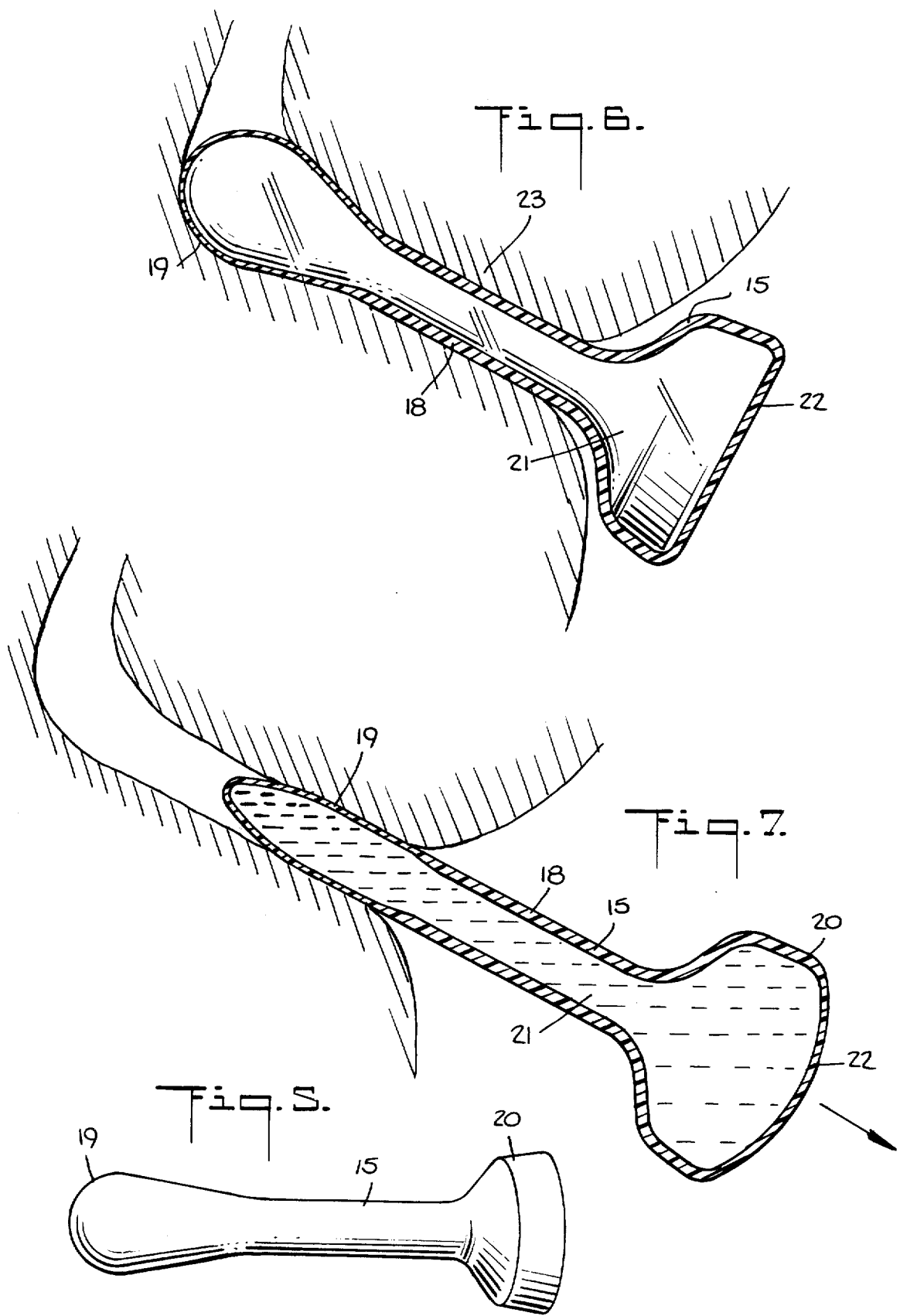

HEMORRHOIDAL DEVICE

BACKGROUND OF THE INVENTION

A common physical disorder that has plagued humans from time immemorial, particularly adult humans, is that of hemorrhoids, a livid and painful swelling formed by vein dilation in the anal cavity or rectum. Many treatments have been devised over the years, including chemical, thermal, electrical and surgical, some involving elaborate treatment procedures and others somewhat drastic, and some of those already mentioned as well as still others having possible damaging side effects. Many of the prior art techniques require administration by trained technicians or, in some cases, physicians.

There has been a long recognized need for a simple inexpensive, non-toxic, self-administered device or procedure that has no possible harmful side effects or after effects and which is completely disposable after a single use. Several attempts have been made, some of these goals have been achieved, but heretofore none has been entirely satisfactory for one or more reasons.

As long ago as 1868 Schevenell et al. in U.S. Pat. No. 77,539 proposed an instrument for treating piles or hemorrhoids involving a tapered hollow electrode of different metals to provide galvanic action when brought into contact with the body fluids, which was claimed to reduce the rectal inflammation. The electrode was to be inserted into the rectal cavity and held in place for several hours in order to achieve the asserted beneficial treatment. Optionally includable within the hollow electrode was a frozen substance. Apart from the prolonged length of required treatment, the other main deficiencies of the device were the need for cleaning and sterilization between uses and the likelihood that the metallic constituents would form toxic acids or salts in contact with body fluids that would enhance, rather than diminish, the bodily disorder.

Another unsuccessful attempt was proposed by Cowie in U.S. Pat. No. 969,134 dated Aug. 30, 1910, who suggested the use of a hollow device, presumably of metal, having a removable screw cap so that crushed ice or other freezing, cooling, or heating medium could be employed. The device of Cowie, albeit some forty or more years after Schevenell et al., did not advance the technology, but rather had the same drawbacks and deficiencies as the proposal of Schevenell et al.

Other more recent efforts have been made to meet this long-felt need, but heretofore no one had devised or even suggested a conveniently packaged, self-administered, completely disposable rectal insert for hemorrhoidal therapy.

BRIEF SUMMARY OF THE INVENTION

Each rectal insert encapsulates a freezable medium and has an elongated tubular body or stem with a relatively small insertable bulbous end and an enlarged non-insertable end constituting a stop member and providing a reservoir for said freezable medium. Both the first said end and a portion of the other end have relatively thin wall sections such that the first said end is collapsible under rectal sphincter pressure when said medium is in the liquid state and said portion of the other end is extensible outwardly to provide compensating additional volume in said reservoir for said liquid upon collapse of the first said end.

DESCRIPTION OF THE DRAWINGS

FIG. 1 is an isometric view of an embodiment of the package of the present invention;

FIG. 2 is an enlarged isometric view of the package shown in FIG. 1;

FIG. 3 is an enlarged fragmentary cross-sectional view taken along lines 3—3 of FIG. 1; and FIG. 4 is an enlarged view of a removed portion of the package shown in FIG. 2.

FIG. 5 is an enlarged isometric view of the rectal insert;

FIG. 6 is an enlarged longitudinal section taken along lines 6—6 of FIG. 5 and shown in the inserted condition;

FIG. 7 is a longitudinal section of the rectal insert shown under retraction conditions.

DESCRIPTION OF THE PREFERRED EMBODIMENT

Referring now to FIGS. 1–4 of the drawings, a package constructed according to the principles of the present invention is shown and designated generally by reference number 10. As shown, said package 10 is comprised of a pair of individual sheets 11 which are preferably each composed of a highly durable, transparent, water-repellent film of polystyrene. Other similar materials may be used as desired.

The sheets 11 have a plurality of complementary pockets or recesses 12 impressed by vacuum forming at spaced positions therealong to provide, when the sheets are joined together as shown in FIGS. 1-3, a corresponding plurality of receptacle portions 13 containing respective receptacles 14, each holding an individual rectal insert 15 to be described in detail hereinafter.

The sheets 11 of the package in assembly may be adhered to one another by heat sealing.

Aligned weakened portions 16 in the sheets 11 constituted by perforations, indentations or the like as shown, are adapted for selective manual separation of each receptacle portion 13 from the rest of the package as desired (see FIG. 2).

The separated portion 17 (see FIG. 4) may then be manipulated as shown to manually separate the sheets 11 and liberate the rectal insert 15 contained in the associated receptacle 14.

As shown in FIGS. 5–7 rectal insert 15 is comprised of an elongated hollow tubular stem portion 18 and bulbous portion 19 of insertable dimensions at one end thereof and a stop or reservoir portion 20 at the other end. Sealed within the insert 15 is liquid 21 (see also FIG. 3) which may be any suitable freezing at or near 0°–32°F., such as, for example, water, ethylene glycol, propylene glycol and mixtures thereof, etc.

Insert 15 is fabricated from low density polyethylene tubing that is extruded with varying wall thicknesses and then blow molded, filled and sealed in accordance with well-known conventional techniques. Low density polyethylene is described, for example in 1973–1974 Modern Plastics Encyclopedia, pp. 78–82 and 550, which is incorporated herein by reference. The entry end 19 and the rearward wall 22 of reservoir end 20 are extruded with thicknesses ranging from about 3 to about 10 mils whereas the remainder of the device has a wall thickness in excess of about 15 mils to provide, after complete fabrication, certain novel features and characteristics that lend exceptional utility and effectiveness to the device.

The particular shape or configuration of the reservoir end 22 may vary as long as it provides the required functions of (a) a stop member limiting the extent of anal insertion and insuring proper positioning during use and (b) a compensating reservoir for giving the desired total cooling capability to the device and compensating for the shift in volume caused by the collapse of the bulbous end 19 to be explained.

The particular shape or configuration of the entry end 19 may also vary so long as it provides (a) enhanced caloric transfer between the treated rectal area and the contained liquid medium and (b) wall collapse in response to rectal pressures upon melting of the frozen liquid to facilitate ultimate withdrawal of the device after completion of the therapeutic treatment as described below.

Stem 18 is generally dimensioned to be about 3 inches in length, about ½ inch in diameter and the stop or reservoir end is usually about ¾ inch or larger in diameter or transverse dimension.

To provide enhanced structural strength in the embodiment shown, the sheets 11 are provided with outwardly and oppositely turned flanged edges 24 along two adjacent edges as shown in FIGS. 1, 2 and 4. Such flanged edges provide gripping portions on the removed receptacle portion as shown in FIG. 4 to enhance manual separation of the two sheets 11 to free the rectal insert 15 for use.

Each package 10 in the embodiment shown is of elongated rectangular configuration to permit insertion thereof in a corresponding rectangular shaped shipping container 25.

In use each package 10 is removed from the shipping container 25 and either as an entity or in one or more severed portions is normally placed in a refrigerating environment before use if the rectal device 15 is to be used in cold therapy.

After freezing of the contained liquid, the sheets 11 of the selected receptacle portion 13 are separated and the stem 18 of the rectal device 15 may be inserted rectally as shown in FIG. 6 for a period of time usually from about 1 to about 6 minutes or longer as desired to achieve beneficial results in alleviating hemorrhoidal discomfort.

In the inserted condition as shown in FIG. 6 bulbous end 19 is disposed internally just beyond the sphincter muscle 23 and dilation of the sphincter muscle during insertion of the device may, in itself, have some beneficial effect on the treatment area since the hemorrhoidal veins span the sphincter muscle.

The reduced wall portion of bulbous portion 19 gives optimum heat transfer between the frozen medium 21 and the treatment area. As the contained medium gradually melts the rectal pressure on bulbous end 19 exerted by the sphincter muscle 23 causes collapse thereof which, because water is incompressible, causes dilation of rear wall 22 of reservoir end 20 (see FIG. 7). The reduction in size of bulbous end 19 facilitates withdrawl of the insert device 15 after completion of the treatment.

It can be seen from the foregoing descriptions that a rectal insert and package are provided affording features that are substantial improvements over prior art devices and which were long sought but not conceived heretofore.

While one embodiment of the invention has been shown and described herein, it is to be understood that changes and additions may be made to the described structures without departing from the scope and spirit of the invention.

What is claimed is:

1. A disposable hollow rectal insert adapted for self-administered treatment of hemorrhoids by cold temperature therapy comprising a unitary molded plastic enclosure containing a freezable medium including an elongated tubular stem portion having enclosed ends and dimensioned for manual rectal insertion at a first of said ends and having an enlarged stop portion at the second of said ends to prevent rectal insertion of the latter, said stem portion adjacent said first end having a relatively thin wall thickness rendering the same collapsible under rectal pressure when said medium is in the liquid state, said stop portion being of bulbous shape and having a relatively thin wall portion being extensible and providing increased internal volume therein to compensate for the collapse of said first end portion under said rectal pressure, said first end portion in the absence of rectal pressure having a bulbous configuration of insertable dimensions.

2. In the insert of claim 1, said freezable medium being a liquid having a freezing point of about 0° to 32°F.

3. An insert according to claim 2 in which said medium is water.

4. An insert according to claim 3 composed of low density polyethylene.

* * * * *